United States Patent [19]

Koyama

[11] Patent Number: 4,884,293
[45] Date of Patent: Nov. 28, 1989

[54] X-RAY PHOTOGRAPHING APPARATUS

[75] Inventor: Katsuhiko Koyama, Ootawara, Japan

[73] Assignee: Kabushiki Kaisha Toshiba, Kawasaki, Japan

[21] Appl. No.: 298,137

[22] Filed: Jan. 18, 1989

[30] Foreign Application Priority Data

Jan. 19, 1988 [JP] Japan .................................. 63-7507

[51] Int. Cl.$^4$ ............................................. G03B 41/16
[52] U.S. Cl. ................................... 378/197; 378/117; 378/193; 378/196
[58] Field of Search ................ 378/193, 177, 195–198, 378/189, 190

[56] References Cited

U.S. PATENT DOCUMENTS

| | | | |
|---|---|---|---|
| 2,822,477 | 11/1951 | Kizaur | 378/193 |
| 3,549,885 | 12/1970 | Andersson | 378/193 |
| 3,659,099 | 4/1972 | Bertheau | 378/193 |
| 4,426,725 | 1/1984 | Grady | 378/196 |
| 4,501,011 | 2/1985 | Hauck et al. | 378/196 |

Primary Examiner—Carolyn E. Fields
Assistant Examiner—Joseph A. Hynds
Attorney, Agent, or Firm—Finnegan, Henderson, Farabow, Garrett and Dunner

[57] ABSTRACT

An X-ray photographing apparatus includes first and second systems for photographing an object from different directions. A first arm of the first system supports a first X-ray tube thereon and is arranged to be rotatable. A second arm of the second system supports a second X-ray tube thereon and is arranged to be rotatable. When at least one of the arms is rotated, interference between the arms is prevented by an interference preventing device. The device has a storing section storing data relating to relative positions between the arms when at least one of the arms is rotated while an iso-center, i.e., the crossing point of X-ray beams emitted from the X-ray tubes coincides with the rotational centers of the arms. When at least one of the arms is rotated while the iso-center shifts from the rotational centers for a distance, a detecting section of the device detects the distance, and an operation section calculates, on the basis of the data and the detected distance, a position where the arms interfere with each other and controls the rotation of the arms according to the calculated interference position. When the arms come near the calculated interference position, the operation section actuates an alarm.

8 Claims, 4 Drawing Sheets

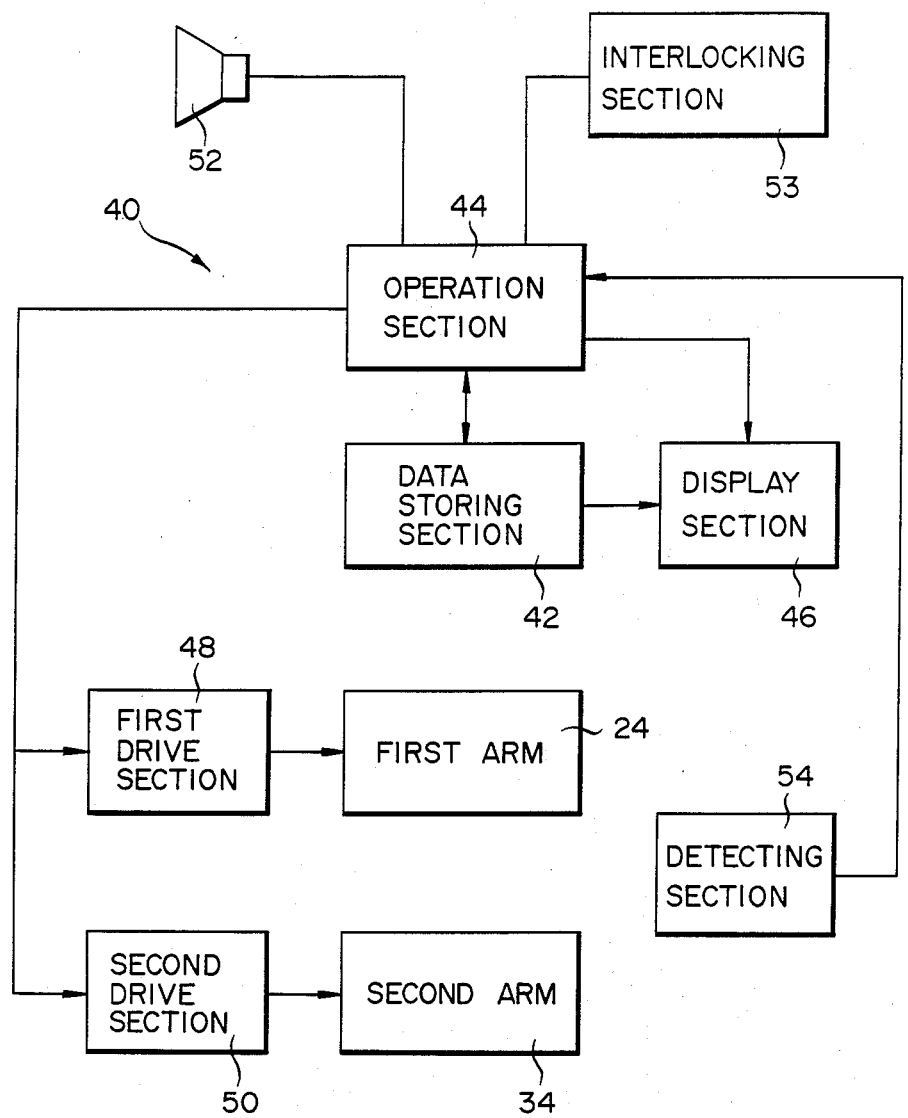
F I G. 5

X-RAY PHOTOGRAPHING APPARATUS

BACKGROUND OF THE INVENTION

1. Field of the Invention

The present invention relates to an X-ray photographing apparatus having a frontal side photographing system positioned to face the frontal side of an object, e.g., a human body to be photographed and a lateral side photographing system positioned to face his lateral side.

2. Description of the Related Art

Recently, X-ray photographing apparatuses of a biplane type, which can photograph an object in various directions, have been proposed as X-ray photographing apparatus used for examination of the circulatory system of the human body, for example.

The photographing apparatus of this type has a frontal side photographing system for photographing the human body from his frontal side and a lateral side photographing system for photographing him from his lateral side and is enable to photograph the human body from two different directions, i.e., from his frontal and lateral sides at the same time.

The frontal side photographing system has a first semicircular (or C-shaped) arm supported by a support shaft which is supported by a base on the floor and extends parallel to the floor. An X-ray tube and an image intensifier (which will be hereinafter referred to as I.I) are rotatably mounted on both ends of the arm, respectively, and opposed to each other. In photographing, the X-ray tube and I.I are adjusted in position so that their central axes are aligned with each other.

The lateral side photographing system has a second semicircular arm which is attached to a support shaft extending perpendicular to the support shaft for the frontal side photographing system. The shaft for the second arm is supported by the ceiling through a carriage which is linearly movable in longitudinal and width directions of the human body to be photographed. An X-ray tube and an I.I are mounted on both ends of the second arm to oppose to each other. When photographing is to be performed, they are adjusted to align their center axes with each other.

When the human body is to be photographed from two directions at the same time, using these photographing systems, they are usually positioned at their normal positions. At their normal positions, they are positioned in such a way that X-ray beams emitted from the X-ray tubes cross each other and that the crossing point or iso-center comes to a reference position where the iso-center coincides with centers of curvature of the first and second arms. When they are under this state, the direction of the X-ray tube and I.I of the frontal side system with respect to the human body is adjusted, by rotating the first arm about its support shaft in LAO (left anterior oblique projection) or RAO (right anterior oblique projection) direction while rotating it about its curvature center in CAU (caudal) or CRA (cranial) direction. Similarly, the direction of the X-ray tube and I.I of the lateral side system is adjusted, by rotating the second arm about its support shaft in CAU or CRA direction while rotating it about its curvature center in LAO or RAO direction. During the above adjustment, the position of the iso-center does not change.

Positions of these X-ray tubes and I.Is are furthrr adjusted relative to the human body, depending upon what his part is to be photographed, by moving the second arm in his longitudinal or width direction by the carriage while moving the first or second arm in a direction perpendicular to the floor by means of its lifter. In this case, the iso-center is shifted from the reference position.

During each of the adjusting processes, each of the arms is moved independently of the other. This creates the possibility that the arms interfere with each other to damage themselves. In order to prevent the interference between the arms, there is provided X-ray photographing apparatuses which have an interference preventing function.

This interference preventing function of the conventional X-ray photographing apparatuses, however, is intended to meet only the case where the first and second arms are rotated in CAU and CRA or RAO and LAO directions, while the arms are held at their normal positions or keeping the iso-center consistent with the reference position. When the first and second arms are rotated while they are out of their normal positions or the iso-center is shifted from the reference position, therefore, their interference cannot be prevented with reliability.

SUMMARY OF THE INVENTION

The present invention has been contrived in consideration of these circumstances, and is intended to provide an X-ray photographing apparatus capable of preventing the arms from interfering with each other even when the arms are adjusted in their positions, with the iso-center being shifted from the reference position.

In order to achieve the above object, according to the present invention, an X-ray photographing apparatus comprises an interference preventing device. The device includes a section for storing data relating to various rotational positions of the first and second arms when the iso-center is at the reference position, a section for detecting a distance the iso-center shifts from the reference position, an operation section for calculating, on the basis of the data stored and the detected distance, that position where the first and second arms interfere with each other when at least one of the arms is to be rotated with the iso-center shifting from the reference position, and means for alarming when the arms come near to the calculated interfering position.

When the first and second arms are adjusted in their positions with the iso-center being shifted from the reference position, therefore, the operator can be previously informed by the interference preventing device that the arms come near to their interfering position and can stop the arms before they interfere with each other. Accordingly, even when the arms are adjusted with the iso-center being shifted from the reference position, they can be surely prevented from interfering with each other.

According to the present invention, in addition to the alarm means, the device may be provided with means for stopping the movement of the arms when they come near to their interfering positions. In this case, even if the operator does not notice the alarm from the alarm means, interference between the arms can be surely prevented.

BRIEF DESCRIPTION OF THE DRAWINGS

FIGS. 1 through 5 show an example of an X-ray photographing apparatus according to the present invention, in which:

FIG. 1 is a side view of the apparatus;

FIG. 2 is a front view of the apparatus;

FIG. 3 is a side view schematically showing a frontal side photographing system;

FIG. 4 is a front view schematically showing a lateral side photographing system; and FIG. 5 is a block diagram showing an interference preventing device.

DETAILED DESCRIPTION OF THE PREFERRED EMBODIMENT

An embodiment of the present invention will now be described in detail with reference to the accompanying drawings.

Figure 1:
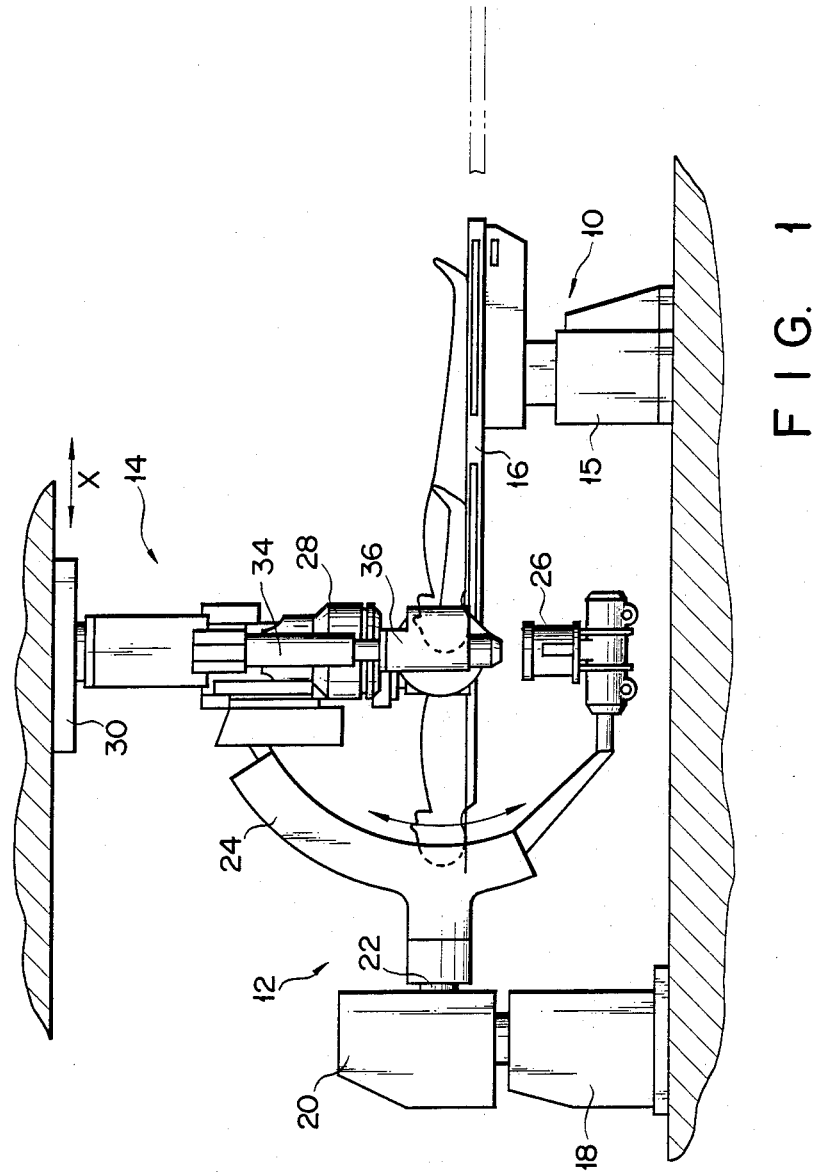
Figure 2:
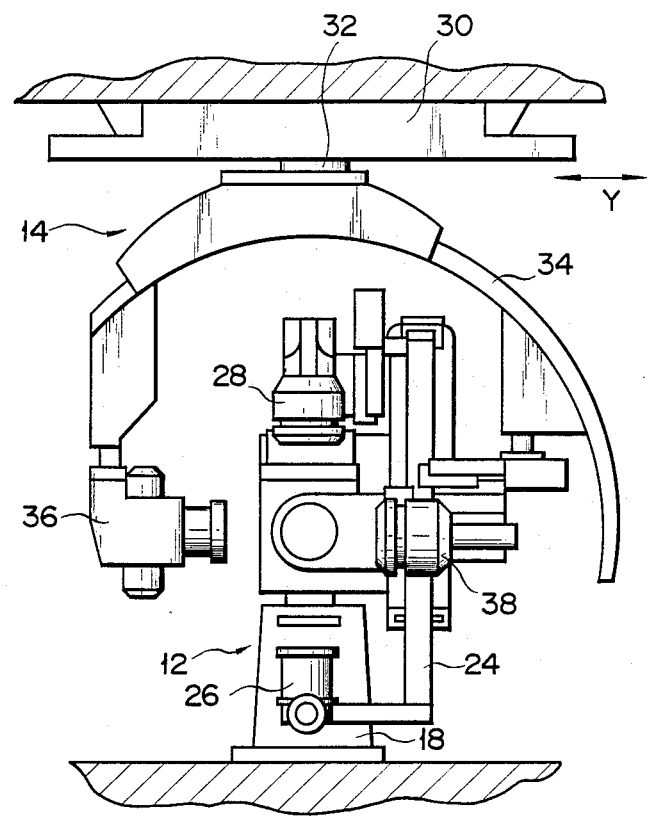

As is shown in FIGS. 1 and 2, an X-ray photographing apparatus includes bed 10 on which a patient to be photographed is laid, frontal side photographing system 12 for photographing the patient from his front side, and lateral side photographing system 14 for photographing him from his lateral side.

Bed 10 includes base 15 placed on the floor and top plate 16 supported by the base to be movable in directions parallel and perpendicular to the floor. Patient 17 to be photographed is laid on plate 16.

Figure 3:
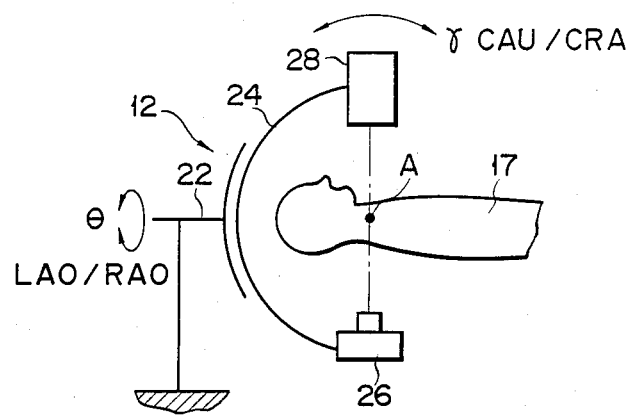

As is shown in FIGS. 1 and 3, frontal side photographing system 12 has base 18 placed on the floor, and support shaft 22 supported by base 18 through support block 20. Support shaft 22 extends horizontally or parallel to the floor and it is supported to be rotatable and extensible in its axial direction by support block 20. First semicircular arm 24 is mounted on support shaft 22 to be rotatable about support shaft 22 by an angle of $\theta$ in LAO and RAO directions. Arm 24 has curvature center A on an extension of the center axis of support shaft 22. It is supported by support shaft 22 to be rotatable along its circumference about curvature center A. In short, arm 24 can rotate by an angle of $\gamma$ in CAU and CRA directions. Arm 24 may be shaped like the letter of C, U or $\Omega$ instead of its semicircular shape.

X-ray tube 26 is attached to one end of arm 24 while image intensifier (I.I) 28 to the other end thereof, and they are opposed to each other. Upon photographing the patient, X-ray tube 26 and I.I 28 are positioned such that their central axes are aligned with each other, passed through curvature center A of arm 24, and located over and under the patient.

Figure 4:
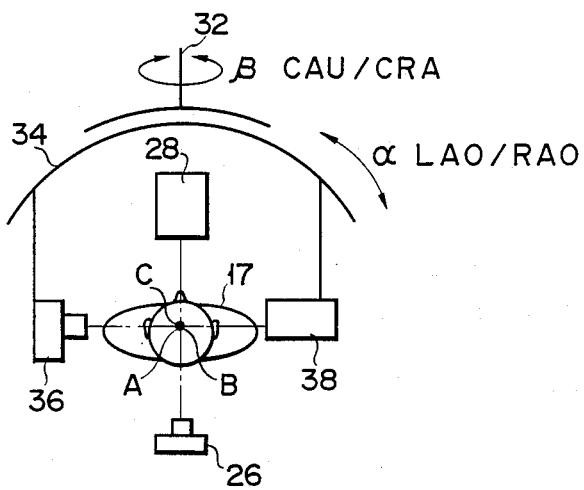

As is shown in FIGS. 1, 2 and 4, lateral side photographing system 14 has carriage 30 attached to the ceiling to be movable on a horizontal plane in the axial direction (or direction X) of support shaft 22 for system 12 and in a direction (or direction Y) perpendicular to the axial direction of support shaft 22. Support shaft 32 is supported by carriage 30 to be rotatable about its axis, and extends in a direction perpendicular to the axis of support shaft 22. Second semicircular arm 34 is attached to support shaft 32 to be rotatable together with support shaft 32 about the axis of shaft 32 by an angle of 8 in CAU and CRA directions. Arm 34 has curvature center B on an extension of the axis of support shaft 32. It is supported by support shaft 32 to be rotatable about curvature center B along its circumference. In short, it can rotate by an angle of $\alpha$ in LAO and RAO directions. Arm 34 may be shaped like the letter of C, U or $\Omega$ instead of its semicircular shape.

X-ray tube 36 is attached to one end of arm 34 while image intensifier (I.I) 38 to the other end thereof, and they are opposite to each other. Upon photographing, X-ray tube 36 and I.I 38 are arranged in such a manner that their central axis align with each other, pass through curvature center B of arm 34, and are located right and left sides of patient 17. Second arm 34 has a radius of curvature larger than that of first arm 24 and is located outside the first arm. Second arm 34 can be lifted up and down in the axial direction of support shaft 32 by a lifter (not shown).

As is shown in FIGS. 1, 2 and 4, in the case of usual photographing, first and second arms 24 and 34 are positioned in such a manner that X-ray beams emitted from X-ray tubes 26 and 36 cross each other and that this crossing point or iso-center C comes to a reference position where iso-center C coincides with curvature centers A and B of the arms. Patient 17 is positioned by bed 12 so that the part of patient which is to be photographed coincides with iso-center C. Under this state, first and second arms 24 and 34 are rotated in CAU/CRA directions and in LAO/RAO directions, respectively, to photograph patient 17 in any desired direction. Depending upon the purpose of photographing, the arms are further adjusted in their positions relative to patient 17, by moving first arm 24 up and down or in the horizontal direction while moving second arm 34 through carriage 30 in direction X or Y and in the vertical direction. When iso-center C is at the reference position, it does not move even if first and second arms 24 and 34 are rotated.

Since each of arms 24 and 34 are rotated independently of the other, there is a fear that the arms may interfere or collide with each other during the rotation. The X-ray photographing apparatus, therefore, has device 40 for preventing arms 24 and 34 from interfering with each other.

As is shown in FIG. 5, device 40 has data storing section 42 storing data relating to relative positions of first and second arms 24 and 34 when the arms are rotated while iso-center C is at the reference position. More specifically, section 42 stores data representing the various positions which first arm 24 takes when it is rotated by the angle $\gamma$ in CAU and CRA directions and rotated by the angle $\theta$ in LAO and RAO directions, and also the various positions which second arm 34 assumes when it is rotated by the angle $\beta$ in CAU and CRA directions and rotated by the angle $\alpha$ in LAO and RAO directions.

Device 40 has operation section 44 which is coupled to section 42. Operation section 44 compiles the data stored in section 42, thereby obtaining the data showing the values which 8 has when arms 24 and 34 interfere with each other, while angles $\alpha$, $\beta$, and $\gamma$ are changed. To be more specific, first arm 24 is rotated 8° in CRA direction, that is $\gamma = 8°$, and second arm 34 is rotated step by step, each time by 8° in CAU direction or CRA direction. Simultaneously, first arm 24 is rotated little by little in LAO and RAO directions, thereby to determine the values which 8 has when arms 24 and 34 interfere with each other. In this case, operation section 44 forms the following table.

UNIT: DEGREE (°)

CRA OF FIRST ARM 5 EQUALS TO (+) 8

| SECOND ARM 14 | CAU | | | | | CRA | | | |
|---|---|---|---|---|---|---|---|---|---|
| | −48 | −40 | −16 | −8 | 0 | 8 | 16 | 40 | 48 |
| LAO 0 | −69 | −69 | −62 | −110 | −110 | −110 | −110 | −110 | −110 |
| (RAO) | −69 | −69 | −62 | −62 | −62 | −62 | −62 | −55 | −53 |
| 8 | −59 | −63 | −110 | −107 | −110 | −110 | −110 | −110 | −110 |
| | −59 | −54 | −55 | −54 | −54 | −54 | −54 | −52 | −50 |
| 16 | −51 | −57 | −102 | −98 | −100 | −105 | −104 | −105 | −106 |
| | −47 | −47 | −46 | −46 | −46 | −46 | −46 | −46 | −45 |
| 24 | −51 | −62 | −90 | −89 | −92 | −96 | −95 | −98 | −100 |
| | −42 | −41 | −38 | −38 | −37 | −37 | −37 | −39 | −40 |
| 80 | −48 | −54 | −32 | −32 | −37 | −40 | −40 | −37 | −39 |
| | 59 | 46 | 22 | 21 | 20 | 19 | 16 | −5 | −12 |
| 88 | −43 | −47 | −24 | −25 | −29 | −32 | −33 | −26 | −27 |
| | 70 | 56 | 30 | 28 | 27 | 26 | 24 | 0 | −7 |
| 112 | 3 | 1 | −2 | −4 | −7 | −8 | −8 | 5 | 6 |
| | 87 | 77 | 53 | 51 | 51 | 51 | 47 | 20 | 6 |
| 120 | 7 | 6 | 0 | −1 | −2 | −2 | −1 | 9 | 9 |
| | 87 | 86 | 61 | 59 | 58 | 58 | 56 | 9 | 9 |

First arm 24 is assumed not to have been rotated in CAU, CRA, LAO, or RAO direction when the X-ray beam emitted from X-ray tube 26 is vertical. Second arm 34 is assumed not to have been rotated in CAR, CRA, LAO or RAO direction when the X-ray beam emitted from X-ray tube 36 is horizontal and at right angles to the axis of support shaft 22.

As is understood from the above table, first arm 24 interferes with second arm 34 when it is rotated −40° and 19° in RAO and LAO directions, respectively, while second arm 34 is rotated 8° and 80° in CRA and LAO directions, respectively.

First arm 24 is rotated step by step, each time by 8° so that operation section 44 forms tables similar to the above one. First arm 24 can rotate at most 35° in CAU direction and at most 45° in CRA direction. Hence, it suffices for section 44 to form 12 tables similar to the above one, thereby to show any and every value that $\theta$ has when arms 24 and 34 interfere with each other, while angles $\alpha$, $\beta$, and $\gamma$ are changed.

When first arm 24 is rotated stepwise in CRA direction, each time by less than 8°, operation section 44 must require more data to form more tables similar to the above table. This is why arm 24 is rotated little by little, each time by 8°. To obtain the value which $\theta$ has when first arm 24 is rotated stepwise, each time by less than 8°, linear approximation is employed.

Interference preventing device 40 has display section 46 connected to data storing section 42 and operation section 44 to thereby display the abovementioned angle data, if necessary.

First arm 24 is rotated and horizontally moved by first drive section 48. Second arm 34 is rotated and horizontally and vertically moved by second drive section 50. These sections 48 and 50 are controlled by operation section 44. Buzzer 52 as alarm means is connected to section 44. When one of the arms comes so near the other as to interfere with each other while they are being rotated, operation section 44 operates buzzer 52 to alarm the operator.

To operation section 44 is connected an interlocking section 53 for stopping the operation of the first and second drive sections. When the arms come near to their interfering position, section 44 actuates the interlocking section, thereby stopping the arms.

When one of such movements as lifting and lowering of first arm 24, lifting and lowering of second arm 34, and moving second arm 34 in directions X and Y is carried out to change the photographing positions of systems 12 and 14, iso-center C shifts from the reference position.

Interference preventing device 40 has detecting section 54, which detects a distance iso-center C shifts from the reference position and inputs the detected distance to operation section 44. Section 44 calculates an interference position where the arms will interfere with each other, considering the distance detected by section 54 together with data in the above-mentioned table.

When first arm 24 is rotated 10° and 8° in LAO and CRA directions, and also second arm 34 is rotated 80° and 8° in LAO and CRA directions, one of the arms can rotate in clockwise 50° (−40° to 10°) and counterclockwise 9° (19° to 10°) until it interferes with the other arm, as can be understood from the above table. The angle of 9°, or interference index 9 (i.e., the angle by which one arm can rotate until it interferes with the other arm) is stored in operation section 44. A required rotational angle of each arm is input to operation section 44 through a keyboard (not shown) or the like, and section 44 calculates the interference index on the basis of the input rotational angle and then memories it.

When iso-center C is shifted above from the reference position for a distance, the distance is detected as a negative value by detecting section 54, and when shifted below from the reference position for a distance, it is detected as a positive value. When iso-center C is lifted 2 cm from the reference position, for example, the distance is detected as −2 and when lowered 1 cm, it is detected as +1. When the value representing the shifting distance is input to operation section 44, section 44 adds the input value to the interference index. When iso-center C is shifted 2 cm above from the reference position, for example, section 44 calculates a new interference index (9−2=) 7, adding the distance −2 to the index 9, and then memories the new index 7. Therefore, section 44 controls the operation of first drive section 48 such that first arm 24 is rotated left within the angle range of 7°. When arm 24 intends to rotate over the angle range, operation section 44 causes buzzer 52 to be sounded to alarm the operator. At the same time, section 44 actuates interlocking section 53 to stop the rotation of arm 24.

According to the X-ray photographing apparatus having the above-described arrangement, the rotation of each of the arms can be controlled in accordance with the distance the iso-center C is shifted from the reference position, when photographing is carried out. As the result, first and second arms 24 and 34 can be prevented from interfering with each other, even when photographing is carried out with iso-center C being shifted from the reference position as well as with iso-center being held at the reference position. When there is caused the fear that the arms will interfere with each other, the interference preventing device actuates alarm means 52 to alarm the operator. Thus, the operator can immediately stop the arms. Even if the operator does not notice the alarm, interlocking section 53 stops the rotation of the arms. Accordingly, interference between the arms can be prevented more surely.

According to the X-ray photographing apparatus of the present invention, the interference between the arms can be reliably prevented without using a large number of interference preventing data.

What is claimed is:

1. An X-ray photographing apparatus comprising:
a first system for photographing an object from a frontal side thereof, said first system including a first arm having a substantially semicircular shape, a first X-ray tube attached to one end of the first arm, a first image intensifier attached to the other end of the first arm and opposed to the first X-ray tube, and first support means for supporting the first arm to be rotatable along its circumference about a rotational center located on an X-ray beam emitted from the first X-ray tube, and to be rotatable about a rotational axis extending in the radial direction of the arm through the rotational center;
a second system for photographing the object from a lateral side thereof, said second system including a second arm having a substantially semicircular shape, a second X-ray tube attached to one end of the second arm, a second image intensifier attached to the other end of the second arm and opposed to the second X-ray tube, and second support means for supporting the second arm to be rotatable along its circumference about a rotational center located on an X-ray beam emitted from the second X-ray tube, and to be rotatable about a rotational axis extending in the radial direction of the second arm through the rotational center;
said first and second arms being supported by the first and second support means to be movable to positions where X-ray beams emitted from the first and second X-ray tubes cross each other and to a reference position where an iso-center defined by said crossing point of the X-ray beams coincides with said rotation centers of the first and second arms;
drive means for rotating and moving the first and second arms; and
means for preventing the first and second arms from interfering with each other when at least one of them is to be rotated, said interfering preventing means including a storing section for storing data relating to relative positions between the first and second arms when at least one of the arms is rotated with the iso-center being held at the reference position, a detecting section for detecting a distance the iso-center shifts from the reference position, an operation section for calculating, on the basis of the data and the detected distance, a position where the first and second arms interfere with each other when at least one of the arms is to be rotated with the iso-center being shifted from the reference position, and driving the drive means in accordance with the calculated interference position, and means for alarming when the first and second arms come near the calculated interference position.

2. An apparatus according to claim 1, wherein said data storing section stores four pieces of data, the first data piece representing the angle said first arm rotates around its rotational center, the second data piece representing the angle said first arm rotates around its rotational axis, the third data piece representing the angle said second arm rotates around its rotation center, and the fourth data piece representing the angle said second arm rotates around its rotational axis; and said operation section uses three of the four data pieces as parameters to form a table of data relating to the remaining data pieces, and drives the drive means according to the table.

3. An apparatus according to claim 2, wherein when at least one of said arms is rotated with the iso-center being shifted from the reference position, said operation section calculates, from the table of data, an interference index which is equivalent to an angle the arm is allowed to rotate until it interferes with the other arm, adds the distance detected by the detecting section, to the interference index, thereby to correct the interference index, and drives the drive means such that at least one of he arms is rotated by an angle less than the angle equivalent to the corrected interference index.

4. An apparatus according to claim 3, wherein said operation section actuates the alarm means when at least one of the arms is likely to rotate through an angle equal to or greater than the angle equivalent to the corrected interference index.

5. An apparatus according to claim 1, wherein said first support means includes a base mounted on the floor and a first support shaft rotatably supported by the base and defining the rotational axis of the first arm, and said first arm is supported by the first support shaft to be rotatable about the rotational center.

6. An apparatus according to claim 5, wherein said second support means includes a carriage attached to the ceiling to be movable in the axial direction of the first support shaft and in a direction perpendicular to the first support shaft, and a second support shaft rotatably supported by the carriage and extending in a direction perpendicular to the first support shaft to define the rotational axis of the second arm, and said second arm is supported b the second support shaft to be rotatable about the rotational center.

7. An apparatus according to claim 1, which further comprises a bed for supporting the object such that part of the object which is to be photographed comes to coincide with the iso-center.

8. An apparatus according to claim 1, wherein said interfering preventing means includes an interlocking means for stopping the drive means when the first and second arms come near the calculated interference position.

* * * * *

UNITED STATES PATENT AND TRADEMARK OFFICE
CERTIFICATE OF CORRECTION

PATENT NO. : 4,884,293
DATED : November 28, 1989
INVENTOR(S) : Katsuhiko Koyama It is certified that error appears in the above-identified patent and that said Letters Patent is hereby corrected as shown below:

```
Claim 3, col. 8, line 31, change "he"
to --the--; and

Claim 6, col. 8, line 53, change "b" to
--by--.
```

Signed and Sealed this

Sixth Day of October, 1992

*Attest:*

DOUGLAS B. COMER

*Attesting Officer*      *Acting Commissioner of Patents and Trademarks*